United States Patent
El-Tahlawy et al.

(10) Patent No.: US 10,463,542 B2
(45) Date of Patent: Nov. 5, 2019

(54) INELASTIC, CONFORMABLE SPORTS TAPE

(71) Applicant: Andover Healthcare, Inc., Salisbury, MA (US)

(72) Inventors: Khaled El-Tahlawy, Portsmouth, NH (US); Thomas S. Murphy, Hillsboro Beach, FL (US)

(73) Assignee: Andover Healthcare, Inc., Salisbury, MA (US)

( * ) Notice: Subject to any disclaimer, the term of this patent is extended or adjusted under 35 U.S.C. 154(b) by 797 days.

(21) Appl. No.: 14/949,987

(22) Filed: Nov. 24, 2015

(65) Prior Publication Data

US 2016/0166440 A1    Jun. 16, 2016

Related U.S. Application Data

(60) Provisional application No. 62/090,176, filed on Dec. 10, 2014.

(51) Int. Cl.
| | | |
|---|---|---|
| *A61F 13/00* | (2006.01) | |
| *C09J 7/21* | (2018.01) | |
| *C09J 133/06* | (2006.01) | |
| *C09J 125/10* | (2006.01) | |
| *C08L 11/00* | (2006.01) | |
| *C08L 75/06* | (2006.01) | |
| *C09D 175/06* | (2006.01) | |
| *B32B 5/28* | (2006.01) | |
| *B32B 27/04* | (2006.01) | |
| *B32B 38/08* | (2006.01) | |
| *A61F 13/02* | (2006.01) | |
| *B32B 5/02* | (2006.01) | |
| *B32B 38/00* | (2006.01) | |

(52) U.S. Cl.
CPC ........ *A61F 13/025* (2013.01); *A61F 13/0273* (2013.01); *A61F 13/0283* (2013.01); *B32B 5/024* (2013.01); *B32B 5/28* (2013.01); *B32B 27/04* (2013.01); *B32B 38/08* (2013.01); *C08L 11/00* (2013.01); *C08L 75/06* (2013.01); *C09D 175/06* (2013.01); *C09J 7/21* (2018.01); *C09J 125/10* (2013.01); *C09J 133/06* (2013.01); *A61F 2013/0028* (2013.01); *B32B 2038/0028* (2013.01); *B32B 2260/046* (2013.01); *B32B 2305/18* (2013.01); *C09J 2425/00* (2013.01); *C09J 2433/00* (2013.01)

(58) Field of Classification Search
None
See application file for complete search history.

(56) References Cited

U.S. PATENT DOCUMENTS

| | | | |
|---|---|---|---|
| 5,762,623 A | 6/1998 | Murphy et al. | |
| 6,048,806 A * | 4/2000 | Deeb | B32B 7/12 442/151 |
| 6,156,424 A | 12/2000 | Taylor | |
| 8,779,230 B2 | 7/2014 | Murphy et al. | |
| 2005/0158539 A1 | 7/2005 | Murphy et al. | |

(Continued)

*Primary Examiner* — Frank D Ducheneaux

(57) ABSTRACT

An athletic tape product for securing or supporting a human or animal body part is provided that includes an elongate, pliable, woven substrate that is stretched in the long direction and impregnated with a water-dispersible polymer, the stretched, impregnated woven substrate further including a coating selected from the group consisting of a cohesive material or an adhesive material. In certain embodiments, the pliable woven substrate is cotton.

18 Claims, 2 Drawing Sheets

(56) References Cited

U.S. PATENT DOCUMENTS

| | | |
|---|---|---|
| 2006/0073328 A1 | 4/2006 | Murphy et al. |
| 2006/0154546 A1 | 7/2006 | Murphy et al. |
| 2007/0259163 A1 | 11/2007 | Connolly et al. |
| 2007/0299383 A1 | 12/2007 | Murphy et al. |
| 2008/0014386 A1 | 1/2008 | Murphy et al. |
| 2008/0014387 A1 | 1/2008 | Murphy et al. |
| 2008/0031931 A1 | 2/2008 | Gunn |
| 2009/0075042 A1 | 3/2009 | Murphy |
| 2010/0055157 A1 | 3/2010 | Gunn |
| 2012/0238933 A1 | 9/2012 | Murphy et al. |
| 2016/0166440 A1 | 6/2016 | El-Tahlawy et al. |
| 2017/0203541 A1 | 7/2017 | El-Tahlawy et al. |
| 2017/0321062 A1 | 11/2017 | Murphy et al. |

\* cited by examiner

INELASTIC, CONFORMABLE SPORTS TAPE

CROSS-REFERENCE TO RELATED APPLICATION

This application claims the priority benefit of U.S. provisional application No. 62/090,176 filed Dec. 10, 2014. The aforementioned application is incorporated herein by reference in its entirety.

BACKGROUND

The present development relates to support tape and, more particularly, to an improved inelastic, conformable support tape. The support tape of the present disclosure may advantageously be used by orthopedists or athletic trainers, to limit the range of motion of a joint to prevent injury or facilitate safe use of an injured body part. The support tape in accordance with this disclosure may be referred to herein variously as "sports tape" or "athletic tape" for the sake of brevity and it will be recognized that the support tape according to the present disclosure may find other uses as well, such as in orthopedic medical applications, veterinary medicine for animal applications, and references to the support tape herein as "sports tape" or "athletic tape" is not intended to exclude such other applications.

Taping of ankles, knees, and elbows is widely used in sports and orthopedic medicine to prevent injury or to protect existing injuries by limiting abnormal or excessive movement and by providing mechanical support to underlying muscles. Currently available athletic tape, such as COACH® athletic tape available from Johnson and Johnson, comprises a woven cotton cloth having a pressure-sensitive adhesive applied to one surface. Such prior art cotton-based tapes are advantageous in that they are highly flexible and conformable to the body part to which they are applied. The prior art cotton cloth tape is also readily hand tearable, which is especially desirable in the case of a sports tape job, which a generally more complex than a simple compression wrap and typically requires tearing multiple strips which are applied in a particular configuration or pattern to provide the desired level of support and immobilization.

Despite its good conformity and hand tearability, it has been found that the prior art cotton tape will stretch significantly, e.g., up to five percent in length, when exposed to moisture, such as exercise-associated sweat and mechanical strain. Under such conditions, these tapes frequently loosen and lose their effectiveness in providing the desired level of orthopedic support to the joint or body part to which it was applied. Another prior art approach is to use a synthetic cloth material in place of the cotton. However, it has been found that synthetic cloth is too stiff and not as conforming to the contours of the body part being taped. Therefore, each of these approaches to athletic or orthopedic taping suffers from one or more shortcomings in comfort and/or performance.

Accordingly, it would be desirable to provide an improved athletic tape for supporting a human or animal body part and method for its manufacture that provides a high degree of flexibility but that does not stretch upon exposure to moisture.

SUMMARY

In accordance with the present disclosure, an athletic tape product for securing or supporting a human or animal body part is provided that includes an elongate, pliable, woven substrate that is stretched in the long direction and impregnated with a water-dispersible polymer, the stretched, impregnated woven substrate further including a coating material selected from the group consisting of a cohesive material or an adhesive material. In certain embodiments, the pliable woven substrate is cotton.

In a further aspect, an athletic tape product for securing or supporting a human or animal body part is provided that includes an elongate, pliable, woven substrate that is stretched in the long direction and including a coating material selected from the group consisting of a cohesive material or an adhesive material. In certain embodiments, the pliable woven substrate is cotton.

In a more limited aspect, the water dispersible polymer is ethylene vinyl acetate (EVA).

In yet another aspect, the present disclosure further includes methods of creating the athletic tape products herein. In general, a first embodiment method involves impregnating a pliable, woven substrate under tension with a first material comprising a water-dispersible polymer and a second material selected from a cohesive material or an adhesive material. A second embodiment method involves a pliable, woven substrate under tension and applying a coating selected from a cohesive material or an adhesive material.

In a first aspect, an athletic tape product for securing or supporting a human or animal body part comprises an elongate, pliable, substrate having a first major surface and a second major surface, the substrate being formed of a woven material that is stretchable in a longitudinal direction between a relaxed state and an elongated state, wherein a longitudinal length of the substrate in the elongated state is greater than the longitudinal length of the substrate in the relaxed state. A polymer material is applied to the substrate, the polymer material affixing the substrate in the elongate state. A coating material is disposed on one or both of the first major surface and the second major surface, the coating material selected from the group consisting of a cohesive material and an adhesive material.

In certain more limited embodiments, the substrate is a textile comprising longitudinal fibers and transverse fibers in a weave pattern.

In certain more limited embodiments, the longitudinal fibers, transverse fibers, or both comprise a material selected from the group consisting of cotton, polyolefin, polyester, and a cotton/synthetic polymer blend.

In certain more limited embodiments, the longitudinal fibers, transverse fibers, or both have a linear mass density of from about 50 deniers to about 500 deniers.

In certain more limited embodiments, the longitudinal fibers are spaced along a transverse axis at a density of from about 20 to about 100 fibers per inch when the substrate is in the relaxed state.

In certain more limited embodiments, the transverse fibers are spaced along a longitudinal axis at a density of from about 15 to about 75 fibers per inch when the substrate is in the relaxed state.

In certain more limited embodiments, the coating material is disposed on the first major surface at a density of from about 40 g/m² to about 150 g/m².

In certain more limited embodiments, the coating material is an adhesive material.

In certain more limited embodiments, the adhesive material comprises a material selected from the group consisting of a styrene-butadiene rubber (SBR) adhesive and an acrylate adhesive.

In certain more limited embodiments, the coating material is a cohesive material.

In certain more limited embodiments, the cohesive material comprises a material selected from the group consisting of polychloroprene, polyester polyurethane, and polycaprolactone polyurethane.

In certain more limited embodiments, the polymer material is a water-dispersible polymer.

In certain more limited embodiments, the substrate is impregnated with the water-dispersible polymer.

In certain more limited embodiments, the substrate is coated with the water-dispersible polymer.

In certain more limited embodiments, the water-dispersible polymer is disposed on the first and second surfaces at a density of from about 10 g/m$^2$ to about 40 g/m$^2$, on a dried weight basis.

In certain more limited embodiments, the water-dispersible polymer is ethylene vinyl acetate.

In certain more limited embodiments, the longitudinal length of the substrate in the elongated state is at least 0.5% greater than the longitudinal length of the substrate in the relaxed state.

In certain more limited embodiments, the substrate is impregnated with the coating material.

In a further aspect, an athletic tape product for securing or supporting a human or animal body part comprises an elongate, pliable, substrate having a first major surface and a second major surface, the substrate being formed of a woven material that is stretchable in a longitudinal direction between a relaxed state and an elongated state. A longitudinal length of the substrate in the elongated state is greater than the longitudinal length of the substrate in the relaxed state and a coating material disposed on one or both of the first major surface and the second major surface. The coating material is selected from the group consisting of a cohesive material and an adhesive material, the coating material affixing the substrate in the elongate state.

In certain more limited embodiments, the substrate is a textile comprising longitudinal fibers and transverse fibers in a weave pattern.

In certain more limited embodiments, the longitudinal fibers, transverse fibers, or both comprise a material selected from the group consisting of cotton, polyolefin, polyester, and a cotton/synthetic polymer blend.

In certain more limited embodiments, the longitudinal fibers, transverse fibers, or both have a linear mass density of from about 50 deniers to about 500 deniers.

In certain more limited embodiments, the longitudinal fibers are spaced along a transverse axis at a density of from about 20 to about 100 fibers per inch when the substrate is in the relaxed state.

In certain more limited embodiments, the transverse fibers are spaced along a longitudinal axis at a density of from about 15 to about 75 fibers per inch when the substrate is in the relaxed state.

In certain more limited embodiments, the coating material is disposed on the first major surface at a density of from about 50 g/m$^2$ to about 200 g/m$^2$.

In certain more limited embodiments, the coating material is an adhesive material.

In certain more limited embodiments, the adhesive material comprises a material selected from the group consisting of a styrene-butadiene rubber (SBR) adhesive and an acrylate adhesive.

In certain more limited embodiments, the coating material is a cohesive material.

In certain more limited embodiments, the cohesive material comprises a material selected from the group consisting of polychloroprene, polyester polyurethane, and polycaprolactone polyurethane.

In certain more limited embodiments, the longitudinal length of the substrate in the elongated state is at least 0.5% greater than the longitudinal length of the substrate in the relaxed state.

In certain more limited embodiments, the substrate is impregnated with the coating material.

In yet another aspect, a method for the manufacture of an athletic tape product includes applying tension to an elongate, pliable, woven substrate along a longitudinal axis thereof to stretch the substrate from a relaxed state to an elongated state wherein a longitudinal length of the substrate in the elongated state is greater than the longitudinal length of the substrate in the relaxed state. The substrate has a first major surface and a second major surface. A dispersion comprising a solvent and a solvent-dispersible polymer is applied to the substrate and the solvent is dried when the substrate is under tension to produce an elongated, polymer treated substrate. A coating material selected from the group consisting of a cohesive material and an adhesive material is applied to one or both of the first major surface and the second major surface of the elongated, polymer treated substrate.

In certain more limited embodiments, the substrate is a textile comprising longitudinal fibers and transverse fibers in a weave pattern.

In certain more limited embodiments, the longitudinal fibers, transverse fibers, or both comprise a material selected from the group consisting of cotton, polyolefin, polyester, and a cotton/synthetic polymer blend.

In certain more limited embodiments, the longitudinal fibers, transverse fibers, or both have a linear mass density of from about 50 deniers to about 500 deniers.

In certain more limited embodiments, the longitudinal fibers are spaced along a transverse axis at a density of from about 20 to about 100 fibers per inch when the substrate is in the relaxed state.

In certain more limited embodiments, the transverse fibers are spaced along a longitudinal axis at a density of from about 15 to about 75 fibers per inch when the substrate is in the relaxed state.

In certain more limited embodiments, the substrate is impregnated with the water-dispersible polymer at a coating density of from about 10 g/m$^2$ to about 40 g/m$^2$.

In certain more limited embodiments, the water-dispersible polymer is ethylene vinyl acetate.

In certain more limited embodiments, the coating material is applied to the first major surface at a coating density of from about 40 g/m$^2$ to about 150 g/m$^2$.

In certain more limited embodiments, the coating material is an adhesive material.

In certain more limited embodiments, the adhesive material comprises a material selected from the group consisting of a styrene-butadiene rubber (SBR) adhesive and an acrylate adhesive.

In certain more limited embodiments, the coating material is a cohesive material.

In certain more limited embodiments, the cohesive material comprises a material selected from the group consisting of polychloroprene, polyester polyurethane, and polycaprolactone polyurethane.

In certain more limited embodiments, the longitudinal length of the substrate in the elongated state is at least 0.5% greater than the longitudinal length of the substrate in the relaxed state.

In certain more limited embodiments, the step of applying a dispersion is selected from the group consisting of coating at least one major surface of the substrate with the dispersion and drying the solvent when the substrate is under tension to produce the elongated, polymer treated substrate; and impregnating the substrate with the dispersion and drying the solvent when the substrate is under tension to produce the elongated, polymer treated substrate.

In certain more limited embodiments, the step of applying a coating material is selected from the group consisting of: spraying at least one major surface of the substrate with the coating material, immersing the substrate in the coating material, and impregnating the substrate with the coating material.

In certain more limited embodiments, the step of applying tension includes passing the substrate around a first roller having a first roller speed and a second roller having a second roller speed, the second roller downstream of the first roller, the second roller speed being selected to create a desired amount of tension in the substrate.

In still another aspect, a method for the manufacture of an athletic tape product comprises applying tension along an elongate, pliable, woven substrate along a longitudinal axis thereof, to stretch the substrate from a relaxed state to an elongated state. A longitudinal length of the substrate in the elongated state is greater than the longitudinal length of the substrate in the relaxed state. The substrate has a first major surface and a second major surface. A coating material is applied to the substrate when the substrate is under tension to produce an elongated, coated substrate, the coating material selected from the group consisting of a cohesive material and an adhesive material.

In certain more limited embodiments, the substrate is a textile comprising longitudinal fibers and transverse fibers in a weave pattern.

In certain more limited embodiments, the longitudinal fibers, transverse fibers, or both comprise a material selected from the group consisting of cotton, polyolefin, polyester, and a cotton/synthetic polymer blend.

In certain more limited embodiments, the longitudinal fibers, transverse fibers, or both have a linear mass density of from about 50 deniers to about 500 deniers.

In certain more limited embodiments, the longitudinal fibers are spaced along a transverse axis at a density of from about 20 to about 100 fibers per inch when the substrate is in the relaxed state.

In certain more limited embodiments, the transverse fibers are spaced along a longitudinal axis at a density of from about 15 to about 75 fibers per inch when the substrate is in the relaxed state.

In certain more limited embodiments, the coating material is applied to the first major surface at a coating density of from about 50 g/m$^2$ to about 200 g/m$^2$.

In certain more limited embodiments, the coating material is an adhesive material.

In certain more limited embodiments, the adhesive material comprises a material selected from the group consisting of a styrene-butadiene rubber (SBR) adhesive and an acrylate adhesive.

In certain more limited embodiments, the coating material is a cohesive material.

In certain more limited embodiments, the cohesive material comprises a material selected from the group consisting of polychloroprene, polyester polyurethane, and polycaprolactone polyurethane.

In certain more limited embodiments, the longitudinal length of the substrate in the elongated state is at least 0.5% greater than the longitudinal length of the substrate in the relaxed state.

In certain more limited embodiments, the step of applying a coating material is selected from the group consisting of spraying at least one major surface of the substrate with the coating material; immersing the substrate in the coating material; and impregnating the substrate with the coating material.

In certain more limited embodiments, the step of applying tension includes passing the substrate around a first roller having a first roller speed and a second roller having a second roller speed, the second roller downstream of the first roller, the second roller speed being selected to create a desired amount of tension in the substrate.

DETAILED DESCRIPTION OF THE PREFERRED EMBODIMENTS

Figure 1:
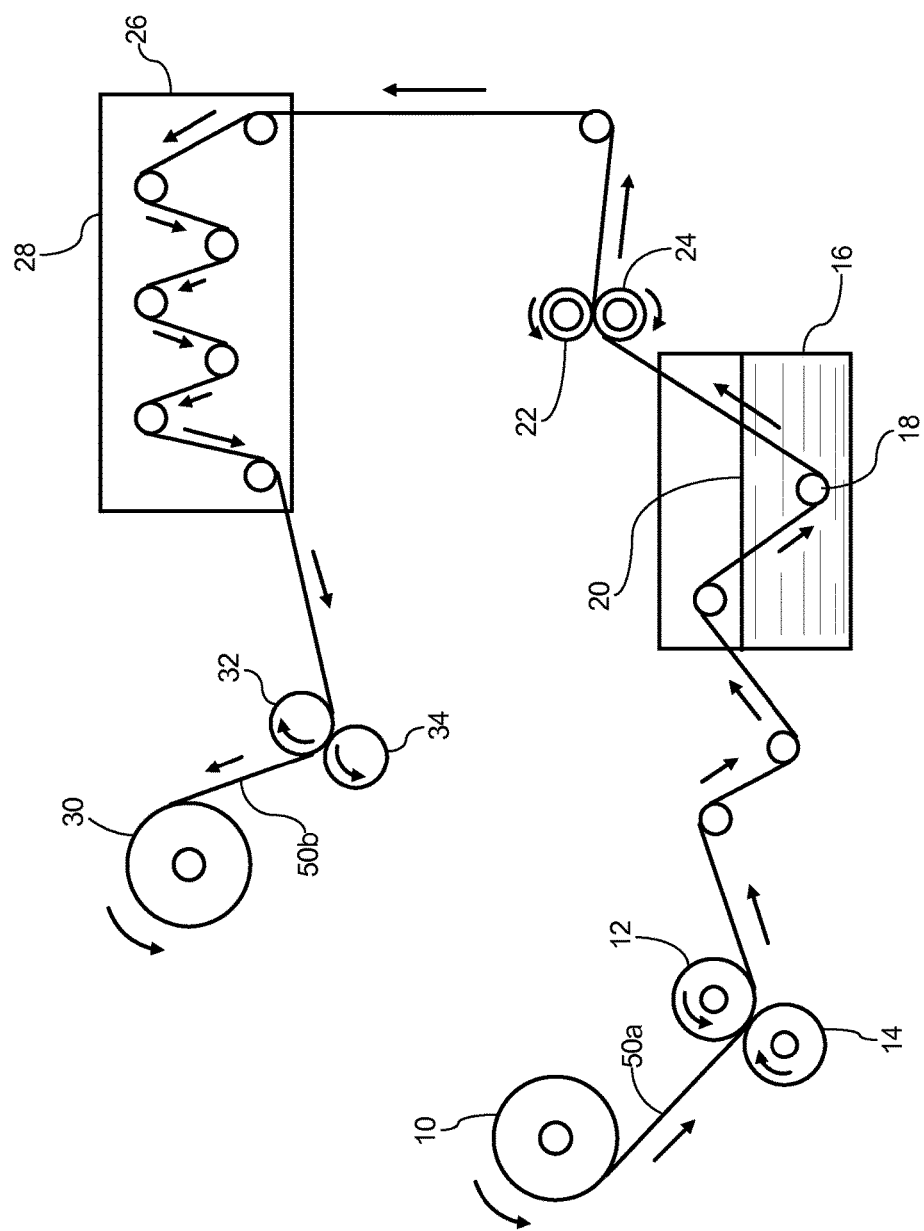
FIG. 1 is a schematic diagram of an exemplary apparatus which may be used to manufacture the athletic tape in accordance with the present invention.

The present disclosure is based, in part, upon the finding that pre-impregnating a cotton fabric with a water dispersible polymer under tension results in an athletic, orthopedic, or veterinary tape with particularly desirable properties, including a high degree of conformability, excellent hand tearability, and improved performance, especially when exposed to exercise induced sweat and mechanical strain.

The athletic support tape herein includes a pliable or conformable woven textile material serving as the substrate for the taping product in accordance with this teaching. The textile material may be formed of fabric comprising warp or longitudinal yarns or threads and weft or transverse yarns or threads crossing the warp yarns or threads in a plain weave pattern. In preferred embodiments, the yarns are formed of spun cotton fibers although materials formed of other natural or synthetic fibers are also contemplated.

In certain embodiments, the warp and/or weft yarns of such suitable hand-tearable substrate tapes may be yarns of cotton, polyolefin, polyester, cotton/synthetic polymer blends, and so forth. In certain cases, warp yarns may be spaced at a density in the range of 20 to 100 yarns per inch measured transversely of the tape, preferably 63 yarns per inch. In certain embodiments, the warp yarns may have a denier in the range of 50 d to 500 d, preferably 150 d. The weft yarns may be spaced at a density in the range of 15 to 75 yarns per inch measured longitudinally of the tape, preferably 44 yarns per inch. In certain embodiments, the weft yarns may have a denier in the range of 50 d to 500 d, preferably 150 d.

Although the present development will be described herein primarily by way of reference to a tape having a width suitable for athletic, orthopedic, or veterinary applications, it will be recognized that the tape may be manufactured in rolls of any width which can then be cut into rolls having the desired width.

The tape product herein may be applied to any human or animal body part. Therefore, in various examples, the body part may be an ankle, a foot, a leg, a knee, an elbow, a forearm, a wrist, a hand, a shoulder, an arm, a thigh, a hip, or a pelvis. Furthermore, the tape product herein is adaptable to both human (e.g., orthopedic medicine or sports medicine) and animal (e.g., veterinary) applications.

Method 1—Two-Step Process

In certain embodiments, the tape product herein is produced using a two-step process, wherein the first step includes pre-coating or pre-impregnating the substrate with a solvent-dispersible synthetic polymer while applying tension to the substrate in the longitudinal direction. The second step includes coating the pretreated substrate with an adhesive or cohesive material.

In certain embodiments, the solvent-dispersible synthetic polymer material is a water-dispersible synthetic polymer. In certain embodiments, the solvent-dispersible synthetic polymer is a hydrophobic polymer.

In preferred embodiments, the synthetic polymer used to pre-coat or pre-impregnate the substrate is Ethylene Vinyl Acetate (EVA). Other synthetic polymers that may advantageously be used to pre-coat or pre-impregnate the substrate include, but are not limited to polyvinyl acetates, polyvinyl alcohols.

It has been found that pre-coating or pre-impregnating the substrate improves the hand tearability of the substrate which improves the ease of application to a subject, particularly where the tape job requires the tearing off and application of multiple, separate segments. It has also been found that the pre-coating or pre-impregnating the substrate reduces the stretchability of the substrate to a minimum, thereby maintaining the desired level of support and compression, even when exposed to sweat and mechanical strain, e.g., induced by the athletic performance of the wearer. In addition, pre-coating or pre-impregnating the substrate with the synthetic polymer under tension has been found increase the hydrophobicity of cotton which, in turn, results in improved moisture vapor transmission and reduced absorption of sweat. Finally, pre-coating or pre-impregnating the substrate with the synthetic polymer under tension has been found to increase the tensile properties of the cloth substrate. In addition, the aforementioned improved properties have been achieved without reducing the softness or conformability of the substrate.

Referring now to FIG. 1, there is shown an exemplary apparatus for the manufacture of the pre-coated or pre-impregnated substrate. The untreated substrate 50a is unwound from a supply roll 10 and travels in the direction indicated and passes through the nip of nip rollers 12 and 14. The substrate passes to a dip tank 16 wherein it passes under a roller 18 is submerged beneath the level of a liquid 20 comprising a synthetic polymer dispersed in a solvent, preferably an aqueous polymer dispersion.

The substrate exits the dip tank 16 and passes through the nip between nip rollers 22 and 24 and then to a dryer 26. The dryer 26 may include a plurality of rollers 28 and may include heating elements, fans, and so forth for evaporating the aqueous/solvent content of the polymer dispersion that has been coated or impregnated onto the substrate. The pre-coated substrate may be dried at a temperature in the range of from 80 degrees C. to about 120 degrees C. The dried, pre-coated or pre-impregnated substrate 50b exits the dryer 26 where it passes through the nip of calendar rollers 32, 34 and is wound onto a wind up roller 30. It will be recognized that the configuration of rollers in FIG. 1 is illustrative and exemplary only and other configurations are contemplated.

The tension may be applied to the substrate in the longitudinal direction via a number of methods. For example, in certain embodiments, tension may be applied by a biasing force, such as a weight or spring force applied to one or more of the rollers. In other embodiments, the tension during the pre-coating or pre-impregnating step may be applied by driving the wind up roller or other roller(s) downstream of the dip tank 16, and in certain embodiments downstream of the dryer 26, at a faster peripheral speed than the nip rollers 12, 14 or other roller(s) upstream of the dip tank 16. An appropriate amount of tension is applied to effect the elongation of the substrate along its longitudinal axis by a specific amount. For example, the tension may cause the substrate to elongate by at least 0.25%, 0.5%, 0.75%, 1%, or more. The pre-coated or pre-impregnated polymer may have a coating density of about 10 to about 40 $g/m^2$, preferably from about 20 to about 28 $g/m^2$, on a dried weight basis.

The pre-coated or pre-impregnated substrate is then coated with either a cohesive material or an adhesive material. In embodiments employing a cohesive material, the cohesive material may be applied to both major surfaces of the substrate. Alternatively, the cohesive material may be applied to one side of the substrate and impregnated through the thickness of the pre-coated substrate to provide a cohesive surface on both major surfaces of the substrate.

Suitable cohesive agents for use in the support tape of the present disclosure include latex-based cohesive agent such as, for example, a natural rubber latex-based cohesive agent. A natural rubber latex-based cohesive agent may contain a mixture of natural rubber modified with one or more tackifying resins. The cohesive agent may also be a synthetic water-based cohesive agent (e.g., in applications in which a latex-free product is desired). Examples of synthetic water-based cohesive agents are described, for example, in commonly assigned Taylor U.S. Pat. No. 6,156,424 ("the Taylor patent"), which is hereby incorporated by reference herein in its entirety. A synthetic water-based cohesive agent may include an elastomer having an inherently crystalline structure and at least one tackifying agent in an amount effective to disrupt the crystalline structure of the elastomer in a partial polycrystalline state such that the elastomer possesses a cohesive property. Such an elastomer may include, for example, polychloroprene, polyester polyurethane, or polycaprolactone polyurethane.

The adhesive or cohesive coating material may be coated at a weight basis of about 40 to about 150 $g/m^2$, preferably from about 85 to about 100 $g/m^2$.

The cohesive material may be applied as an aqueous dispersion or emulsion to both major surfaces of the pre-treated tape, e.g., using a dip dank and nip roller apparatus as shown in FIG. 1. Alternatively, the cohesive material may be applied to both major surfaces as an aqueous emulsion or dispersion by spraying or coating and drying. In certain embodiments, the cohesive material may be applied to both major surfaces of the substrate as a viscid mass, coatable syrup, or sprayable liquid and spread with rollers or spreader blades. In certain embodiments, the polymer pre-coating and the cohesive material may be applied batch wise, in separate steps. Alternatively, the pre-coated polymer and the cohesive material may be applied in a continuous process. For example the cohesive material may be applied to a major surface of the substrate as it exits the dryer 26 (see FIG. 1).

Figure 2:
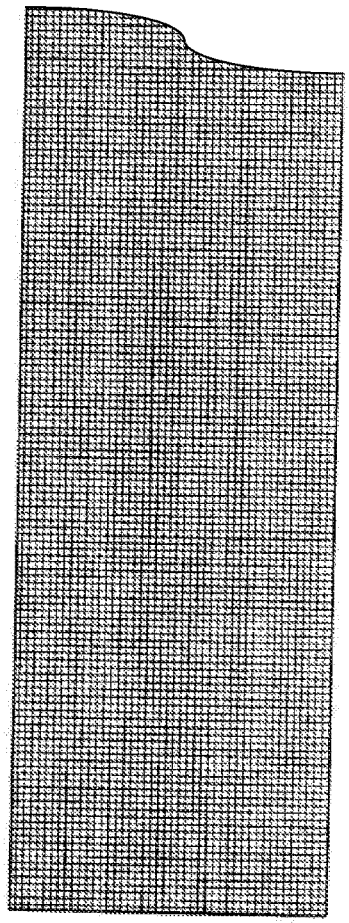
FIG. 2 is a fragmentary, top plan view of a strip of sports tape formed in accordance with the present disclosure.
Figure 3:
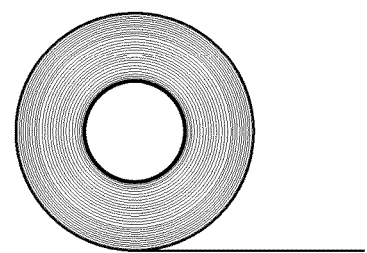
FIG. 3 is a side elevational view of a roll of sports tape formed in accordance with the present disclosure.

A fragmentary, top plan view of a strip of sports tape formed in accordance with the present disclosure appears in FIG. 2. A side elevational view of an exemplary roll of sports tape formed in accordance with the present disclosure appears in FIG. 3.

Table 1 illustrates an exemplary non-latex cohesive formulation for coating the pre-coated or pre-impregnated substrate.

TABLE 1

| Material | % by Weight |
| --- | --- |
| Polychloroprene | 25-75, preferably 50 |
| Tackifier I (Modified Rosin ester) | 5-20, preferably 13 |
| Tackifier II (Rosin Ester) | 15-25, preferably 20 |
| Preservative | 0-3, preferably 1 |
| Water | 10-25, preferably 16 |
| Other (filler, pigments, antimicrobial agent, etc.) | 0-10, preferably 4 |

Table 2 illustrates an exemplary latex-based cohesive formulation for coating the pre-coated or pre-impregnated substrate.

TABLE 2

| Material | % by Weight |
| --- | --- |
| Natural Rubber Latex | 25-75, preferably 56 |
| Tackifier I (Rosin ester) | 5-25, preferably 17 |
| Tackifier III (Rosin Ester) | 5-15, preferably 7 |
| Preservative | 0-3, preferably 1 |
| Water | 10-25, preferably 15 |
| Other (filler, pigments, antimicrobial agents, etc.) | 0-10, preferably 4 |

In embodiments employing an adhesive coating, the adhesive may be applied to one major surface of the substrate. In certain embodiments, the adhesive is a pressure sensitive adhesive (PSA), and may be, for example, styrene-butadiene rubber (SBR), acrylate (e.g., alkyl acrylate) based PSA's and the like. In certain embodiments, a backsize or release coating containing a release agent, such as a silicone release agent may be applied to the surface of the substrate opposite the adhesive coating to prevent or diminish self-adhesion of the tape when it spooled on a roll.

The adhesive material may be applied, for example, by applying the adhesive material to a major surface of the substrate as a viscid mass, coatable syrup, or sprayable liquid and winding the substrate through the nip of a pair of nip rollers or between a roller an adjacent spreader blade. In certain embodiments, the adhesive material may be applied in an application step which is separate from the pre-coating or pre-impregnating step. Alternatively, the pre-coated polymer and the adhesive material may be applied in a single winding step. For example the adhesive material may be applied to a major surface of the substrate as it exits the dryer 26 (see FIG. 1).

Table 3 illustrates an exemplary acrylate-based adhesive formulation for coating the pre-coated or pre-impregnated substrate.

TABLE 3

| Material | % by Weight |
| --- | --- |
| Acrylate PSA | 70-90, preferably 78 |
| Tackifier II | 10-30, preferably 20 |
| Preservative | 0-3, preferably 1 |
| Thickener | 0.5-3, preferably 1 |

Table 4 illustrates an exemplary styrene butadiene rubber-based adhesive formulation for coating the pre-coated or pre-impregnated substrate.

TABLE 4

| Material | % by Weight |
| --- | --- |
| SBR-I | 20-60, preferably 40 |
| SBR-II | 10-30, preferably 20 |
| Tackifier II | 5-25, preferably 15 |
| Thickener | 0.5-3, preferably 1 |

Example 1

An aqueous dispersion was made by mixing 50 g of EVA with 50 g of water. Natural cotton cloth was used having plain weave pattern with a warp yarn density of 63 yarns per inch and a weft yarns density of 44 yarns per inch, the cloth having a warp denier of 150 d and a weft denier of 150 d. The untreated cloth had a tensile strength of 25 lb/inch to break in the warp direction, an elongation of 2.8% of the original length in the warp direction, and a front-to-back peel force of 0 oz./inch (peel angle of 180 degrees), as measured by ASTM D3330/D3330M-04 (2010) (*Standard Test Method for Peel Adhesion of Pressure-Sensitive Tape*).

The untreated cotton cloth was unwound from a supply roll and passed through the nip of nip rollers. The cotton cloth passed to a dip tank wherein it passed under a roller and was submerged beneath the level of the liquid comprised of the EVA aqueous dispersion. The substrate exited the dip tank and passed through the nip between nip rollers and then to a dryer. The dried, EVA-coated cotton cloth exited the dryer and was wound onto a wind up roller.

The EVA-coated and dried cotton cloth had a coating weight of 25 $g/m^2$, a tensile strength of 38 lb/inch to break in the warp direction, an elongation of 0.5% of the original length in the warp direction, and a front-to-back peel force of 0 oz./inch (peel angle of 180 degrees), as measured by ASTM D3330/D3330M-04 (2010).

A cohesive aqueous dispersion was made by mixing 56 g of natural rubber latex, 17 g Tackifier I (Rosin ester), 7 g Tackifier III (Rosin Ester), 1 g preservative, 4 g of other fillers, pigments, etc. and 15 g water to yield a cohesive aqueous dispersion The composition was coated onto both sides of the EVA-coated cotton cloth as follows. The EVA-coated cotton cloth was unwound from a supply roll and passed through the nip of nip rollers. The EVA-coated cotton cloth passed to a dip tank wherein it passed under a roller and was submerged beneath the level of the liquid comprised of the cohesive aqueous dispersion. The substrate exited the dip tank and passed through the nip between nip rollers and then to a dryer. The dried, coated cotton cloth exited the dryer and was wound onto a wind up roller.

The cohesive tape had a coating weight of 95 $g/m^2$ of the cohesive composition, a tensile strength of 43 lb/inch in the warp direction, an elongation of 0.5% of the original length in the warp direction, and a front-to-back peel force of 25 oz./inch (peel angle of 180 degrees), as measured by ASTM D3330/D3330M-04 (2010).

Method 2—One-Step Process

In certain embodiments, one or both major surfaces of a textile substrate are coated with a cohesive material while the substrate is under tension. The cohesive material may be as detailed above, and may be a natural rubber latex cohesive agent or a synthetic cohesive agent. The cohesive material may be applied directly to both major surfaces of the substrate. Alternatively, the cohesive material may be applied to one side of the substrate and impregnated through the thickness of the substrate to provide a cohesive surface on both major surfaces of the substrate. The cohesive material may be applied, for example, by applying the cohesive material as a viscid mass and winding the substrate through the nip of a pair of nip rollers or between rollers having adjacent spreader blades. Alternatively, the cohesive material may be applied as an aqueous dispersion or emulsion, e.g., via a dip tank and nip rollers, spray coating, etc.

In certain embodiments, the cohesive material is coated at a weight basis of about 50 to about 200 g/m$^2$, preferably from about 100 to about 130 g/m$^2$ and dried after application to remove moisture. In certain embodiments, the percentage of solids in the cohesive material is in the range of from about 30% to about 60% by weight and preferably is in the range of from about 50% to about 60% by weight.

Example 2

A cohesive aqueous dispersion was made as described above in Example 1 and the composition was coated onto both sides of untreated plain weave cotton cloth having warp and weft yarn density and denier as described in Example 1. The untreated cotton cloth was unwound from a supply roll and passed through the nip of nip rollers. The untreated cotton cloth passed to a dip tank wherein it passed under a roller and was submerged beneath the level of the liquid comprised of the cohesive aqueous dispersion. The substrate exited the dip tank and passed through the nip between nip rollers and then to a dryer. The dried, coated cotton cloth exited the dryer and was wound onto a wind up roller. The cohesive tape had a coating weight of 95 g/m$^2$ of the cohesive composition.

It will be understood that the foregoing is only illustrative of the principles of the present invention, and that still other modifications can be made by those skilled in the art without departing from the scope and spirit of the invention. For example, the various materials mentioned herein are only examples, and other materials possessing similar properties can be used, if desired.

What is claimed is:

1. An athletic tape product for securing or supporting a human or animal body part, the product comprising:
    an elongate, pliable, substrate having a first major surface and a second major surface, the substrate being formed of a woven material that is stretchable in a longitudinal direction between a relaxed state and a stretched state, wherein a longitudinal length of the substrate in the stretched state is greater than the longitudinal length of the substrate in the relaxed state;
    a polymer material applied to the substrate, the polymer material affixing the substrate in the stretched state; and
    a coating material disposed on one or both of the first major surface and the second major surface, the coating material selected from the group consisting of a cohesive material and an adhesive material.

2. The athletic tape product of claim 1, wherein the substrate is a woven material comprising longitudinal fibers extending in the longitudinal direction and transverse fibers extending transversely with respect to the longitudinal direction.

3. The athletic tape product of claim 2, wherein the longitudinal fibers, transverse fibers, or both comprise a material selected from the group consisting of cotton, polyolefin, polyester, and a cotton/synthetic polymer blend.

4. The athletic tape product of claim 2, wherein the longitudinal fibers, transverse fibers, or both have a linear mass density of from about 50 deniers to about 500 deniers.

5. The athletic tape product of claim 2, wherein the longitudinal fibers are spaced along a transverse axis at a density of from about 20 to about 100 fibers per inch when the substrate is in the relaxed state.

6. The athletic tape product of claim 2, wherein the transverse fibers are spaced along a longitudinal axis at a density of from about 15 to about 75 fibers per inch when the substrate is in the relaxed state.

7. The athletic tape product of claim 1, wherein the coating material is disposed on the first major surface at a coating density of from about 40 g/m$^2$ to about 150 g/m$^2$.

8. The athletic tape product of claim 1, wherein the coating material is an adhesive material.

9. The athletic tape product of claim 8, wherein the adhesive material comprises a material selected from the group consisting of a styrene-butadiene rubber (SBR) adhesive and an acrylate adhesive.

10. The athletic tape product of claim 1, wherein the coating material is a cohesive material.

11. The athletic tape product of claim 10, wherein the cohesive material comprises a material selected from the group consisting of polychloroprene, polyester polyurethane, and polycaprolactone polyurethane.

12. The athletic tape product of claim 1, wherein the polymer material is a water-dispersible polymer.

13. The athletic tape product of claim 12, wherein the substrate is impregnated with the water-dispersible polymer.

14. The athletic tape product of claim 12, wherein the substrate is coated with the water-dispersible polymer.

15. The athletic tape product of claim 12, wherein the water-dispersible polymer is disposed on the first and second major surfaces at a coating density of from about 10 g/m$^2$ to about 40 g/m$^2$, on a dried weight basis.

16. The athletic tape product of claim 12, wherein the water-dispersible polymer is ethylene vinyl acetate.

17. The athletic tape product of claim 1, wherein the longitudinal length of the substrate in the stretched state is at least 0.5% greater than the longitudinal length of the substrate in the relaxed state.

18. The athletic tape product of claim 1, wherein the substrate is impregnated with the coating material.

* * * * *